United States Patent [19]

Pittman

[11] Patent Number: 5,310,084
[45] Date of Patent: May 10, 1994

[54] COMBINATION CONDOM WARMING AND RADIO APPARATUS

[76] Inventor: Daniel J. Pittman, 236 3rd St. #8, Juneau, Ak. 99801

[21] Appl. No.: 75,612

[22] Filed: Jun. 14, 1993

[51] Int. Cl.⁵ .............................................. G07F 11/72
[52] U.S. Cl. .................. 221/150 A; 221/199; 221/232; 221/268
[58] Field of Search ............ 221/150 R, 150 A, 226, 221/232, 268, 199; 222/146.2, 146.5, 192

[56] References Cited

U.S. PATENT DOCUMENTS

| | | | |
|---|---|---|---|
| 3,055,547 | 9/1962 | Radcliffe et al. | 221/232 |
| 3,191,588 | 6/1965 | Thew | 221/232 X |
| 3,578,207 | 5/1971 | Danow | 221/232 |
| 4,101,053 | 7/1978 | Mast, Jr. | 221/232 |
| 4,700,048 | 10/1987 | Levy | 221/150 AX |
| 4,759,468 | 7/1989 | Hoffman | 221/131 X |
| 4,890,205 | 12/1989 | Schaffer | 221/150 A X |
| 5,000,343 | 3/1991 | Allen | 221/199 X |

Primary Examiner—Robert P. Olszewski
Assistant Examiner—Dean A. Reichard
Attorney, Agent, or Firm—Leon Gilden

[57] ABSTRACT

A clock radio housing is arranged to include spaced chambers, with an underlying chamber directing heat to an overlying chamber having a row of condoms directed to a second side wall of the housing, wherein a push-bar projecting through a top wall of the housing is oriented to direct condom packages one at a time through a second side wall chute.

3 Claims, 4 Drawing Sheets

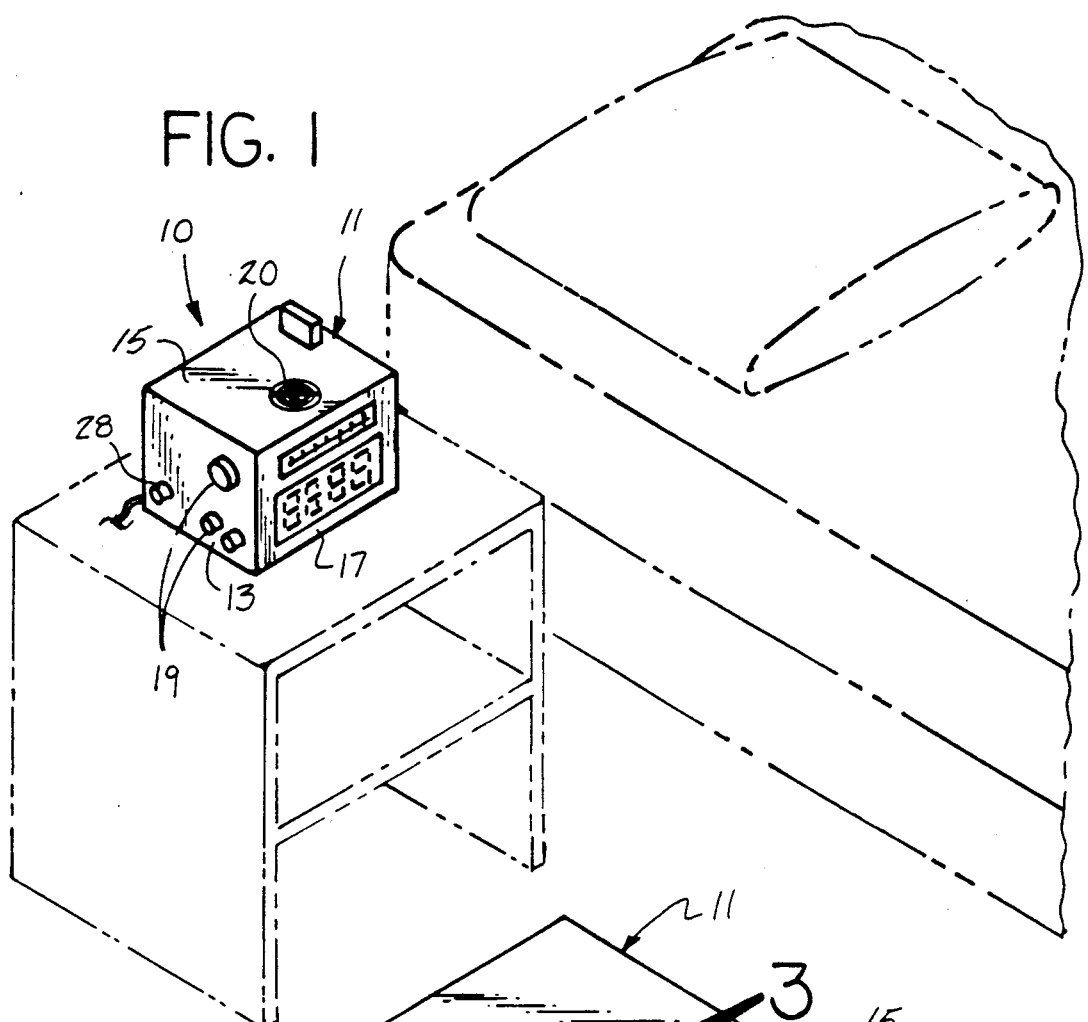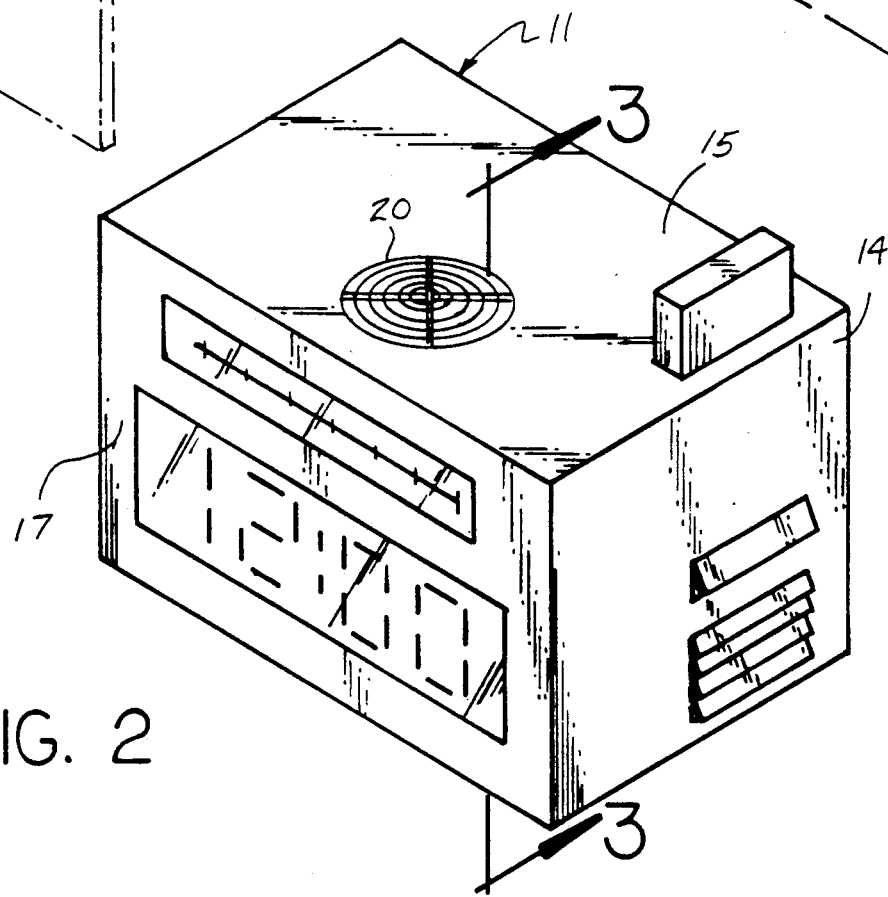

COMBINATION CONDOM WARMING AND RADIO APPARATUS

BACKGROUND OF THE INVENTION

1. Field of the Invention

The field of invention relates to condom apparatus, and more particularly pertains to a new and improved combination condom warming and radio apparatus wherein the same is directed to employing a condom warming chamber structure in association with an entertainment structure configured as a radio.

2. Description of the Prior Art

The instant invention is directed to improvements in the prior art by utilizing a heat imparting chamber within a radio structure configured as an entertainment module to include the warming of condom packages in geographical regions of wintry temperatures. To this end, the instant invention overcomes deficiencies not heretofore addressed in the prior art relative to such geographical areas and in this respect, the present invention substantially fulfills this need.

SUMMARY OF THE INVENTION

In view of the foregoing disadvantages inherent in the known types of condom container structure now present in the prior art, the present invention provides a combination condom warming and radio apparatus wherein the same is directed to the warming of individual condom containers and orienting such packages for projecting relative to a unitary housing. As such, the general purpose of the present invention, which will be described subsequently in greater detail, is to provide a new and improved combination condom warming and radio apparatus which has all the advantages of the prior art condom container apparatus and none of the disadvantages.

To attain this, the present invention provides a clock radio housing arranged to include spaced chambers, with an underlying chamber directing heat to an overlying chamber having a row of condoms directed to a second side wall of the housing, wherein a push-bar projecting through a top wall of the housing is oriented to direct condom packages one at a time through a second side wall chute.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved combination condom warming and radio apparatus which has all the advantages of the prior art condom apparatus and none of the disadvantages.

It is another object of the present invention to provide a new and improved combination condom warming and radio apparatus which may be easily and efficiently manufactured and marketed.

It is a further object of the present invention to provide a new and improved combination condom warming and radio apparatus which is of a durable and reliable construction.

An even further object of the present invention is to provide a new and improved combination condom warming and radio apparatus which is susceptible of a low cost of manufacture with regard to both materials and labor, and which accordingly is then susceptible of low prices of sale to the consuming public, thereby making such combination condom warming and radio apparatus economically available to the buying public.

Still yet another object of the present invention is to provide a new and improved combination condom warming and radio apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularly in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the invention.

FIG. 2 is an enlarged isometric illustration of the invention.

DESCRIPTION OF THE PREFERRED EMBODIMENT

Figure 3:
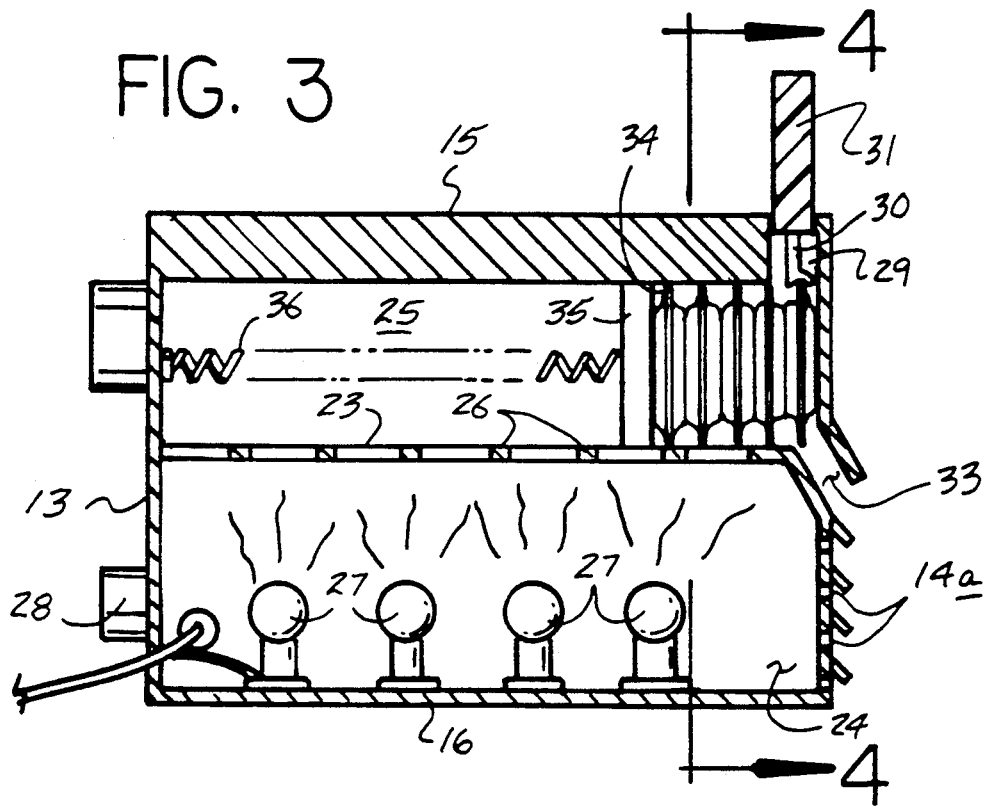
FIG. 3 is an orthographic view, taken along the lines 3—3 of FIG. 2 in the direction indicated by the arrows.
Figure 4:
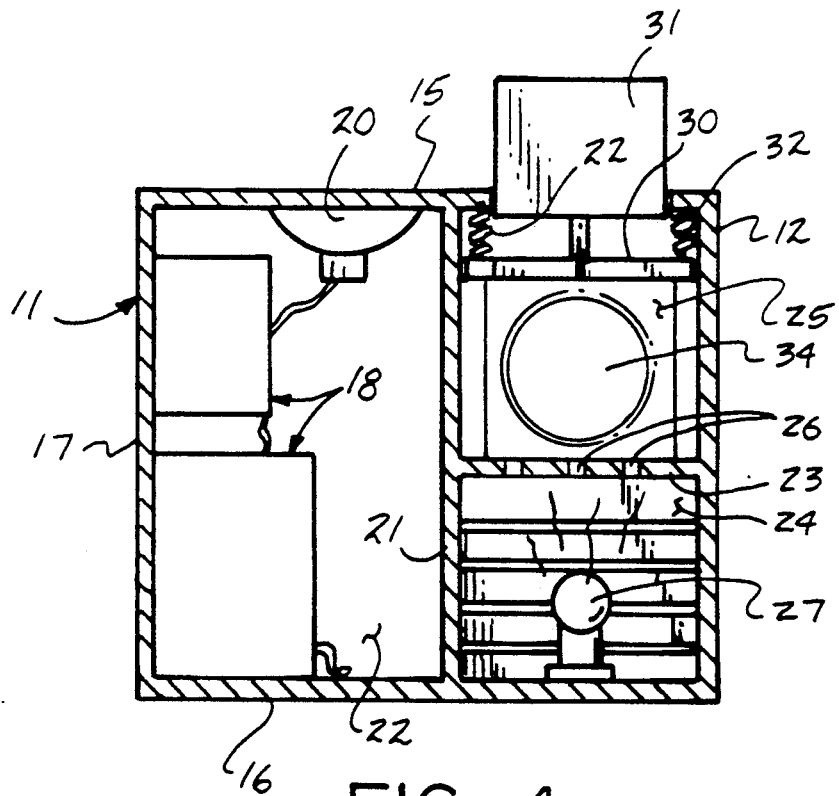
FIG. 4 is an orthographic view, taken along the lines 4—4 of FIG. 3 in the direction indicated by the arrows.

With reference now to the drawings, and in particular to FIGS. 1 to 8 thereof, a new and improved combination condom warming and radio apparatus embodying the principles and concepts of the present invention and generally designated by the reference numeral 10 will be described.

More specifically, the combination condom warming and radio apparatus 10 of the instant invention essentially comprises a radio organization arranged in combination with a condom dispenser construction to provide for a unitary housing oriented for ease of use and in association with an amusement function, as exemplified by the radio, wherein the unitary housing 11 includes a rear wall 12 spaced from a front wall 17, a first side wall 13 spaced from a second side wall 14, and a top wall 15 spaced from a bottom wall 16. A clock radio member 18 of conventional configuration is mounted within a first chamber 22 (see FIG. 4) within the housing 11. First side wall clock radio controls 19 are provided and directed through the first side wall, to include a tuner dial, an on/off switch, and a volume control and the like, as well as required controls for setting a clock radio per se, as is known in the prior art. An intermediate wall 21 is mounted within the housing 11 between the front wall 17 and the rear wall 12 defining the first chamber 22 as noted, and a second and third chamber 24 and 25 that are divided by a partition wall 23 having partition wall apertures 26 (see FIGS. 3 and 4) in communication between the second and third chambers 24 and 25. A plurality of radiant heat lamps 27 are mounted within the second chamber, and having vented side wall openings 14a, as indicated in FIG. 3, to direct convection flow into the second chamber 24 that is heated and direct such heat into the third chamber through the apertures 26. A row of condom package units 34 are accordingly mounted within the third chamber, with an abutment plate 35 having an abutment plate spring 36 interposed between the abutment plate and the first wall 13 to direct the condom package units 34 against the second wall 14, wherein a second side wall chute 33 is directed from the partition wall 23 through the chute and exteriorly of the second side wall 14. To project individual condom package units 34 through the chute 33, a push bar 30 is mounted within a top wall slot 29 that is positioned in adjacency to the second side wall 14 and over the chute 33, with the push bar having a push bar handle 31 directed through the slot 29 and projecting beyond the top wall 15 for manual access thereto, whereupon projection of the handle 31 against the push bar springs 32 that are secured between the push bar and the top wall 15 normally biasing the push bar in adjacency to the top wall.

Figure 5:
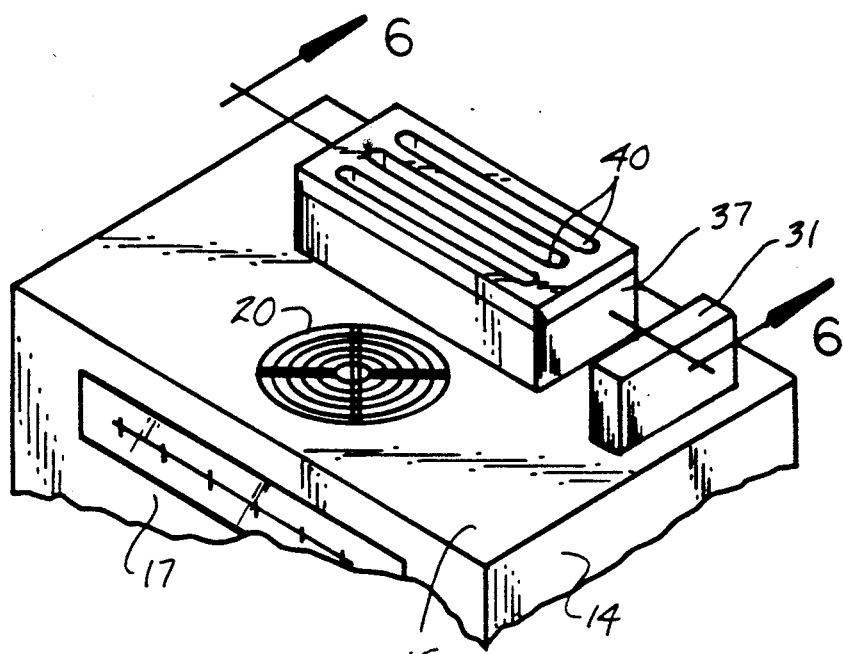
FIG. 5 is an isometric illustration of a top wall, including an aromatic fluid reservoir.
Figure 6:
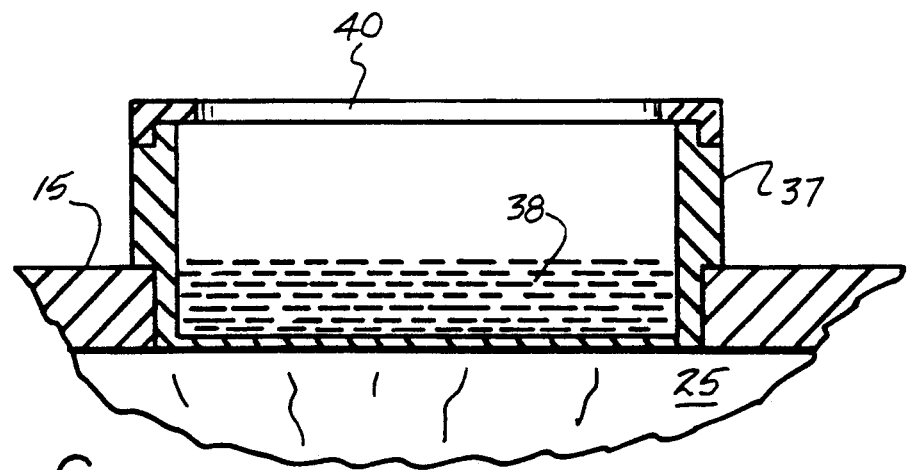
FIG. 6 is an orthographic view, taken along the lines 6—6 of FIG. 5 in the direction indicated by the arrows.

The FIGS. 5 and 6 indicate the use of a reservoir container 37 mounted to the top wall, having a metallic construction of heat transmissible material, wherein an aromatic fluid 38 contained within the reservoir container 37 is heated to direct such aromatic fluid in a vaporized state through lid apertures 40 directed through the reservoir lid.

Figure 7:
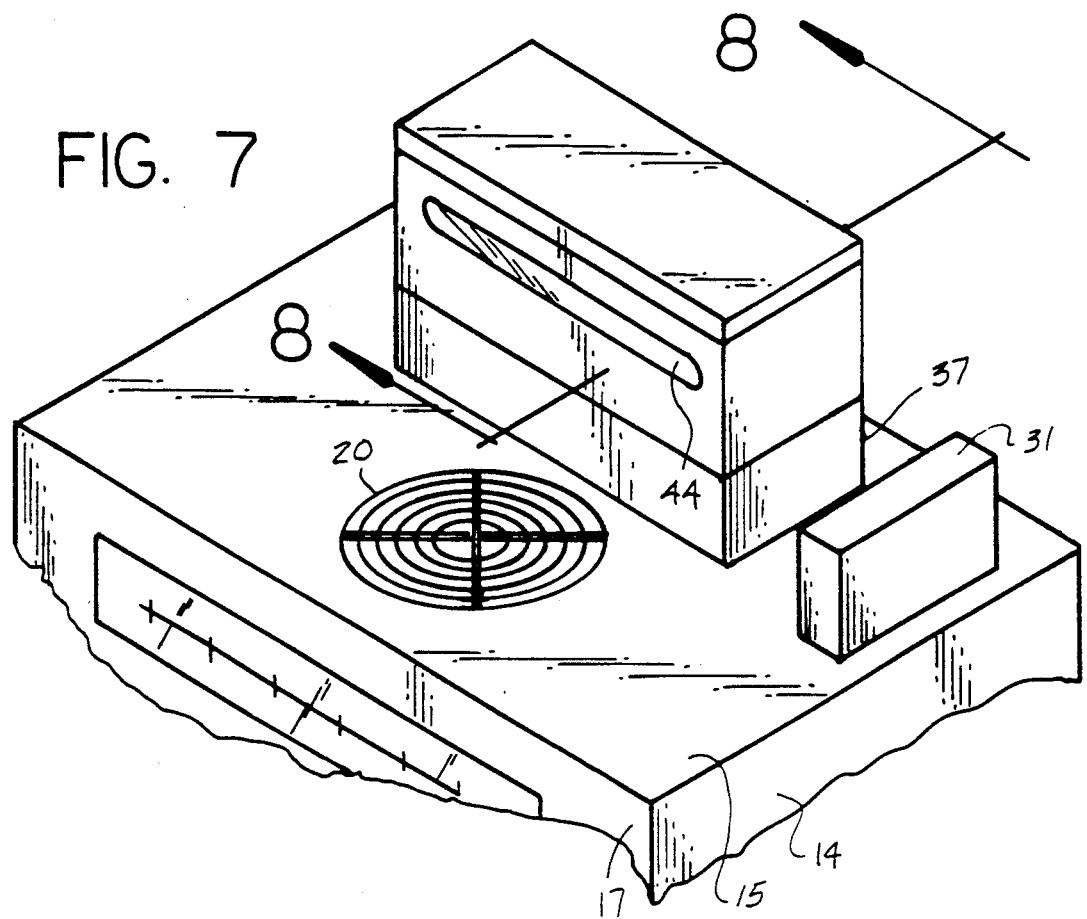
FIG. 7 is an isometric illustration of a modified reservoir housing, of a type as indicated in FIG. 6.
Figure 8:
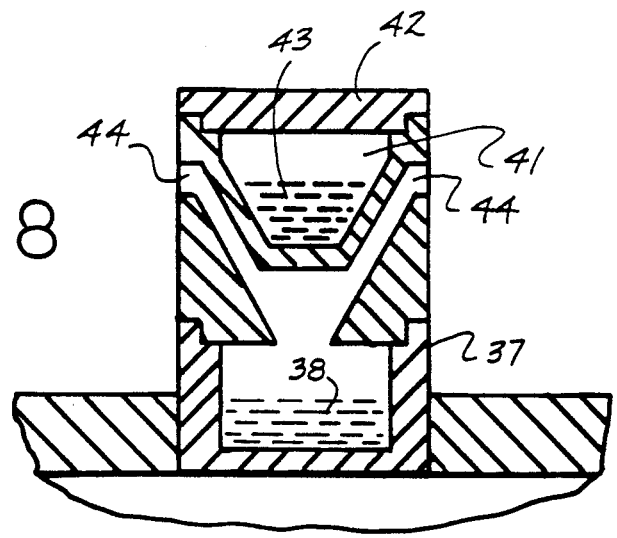
FIG. 8 is an orthographic view, taken along the lines 8—8 of FIG. 7 in the direction indicated by the arrows.

The FIGS. 7 and 8 indicate the use of a lid chamber 41 in lieu of the lid, such as the lid chamber 41, including a second lid 42 mounted thereon to contain and effect heating of a body oil 43 therewithin, wherein lid chamber slots 44 are directed through the lid chamber 41 from the reservoir container 37 directing the vaporized aromatic fluid 38 through the lid chamber slots 44.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A combination condom warming and radio apparatus, comprising, a unitary housing, having a rear wall spaced from a front wall, a bottom wall spaced from a top wall, and a first side wall spaced from a second side wall, wherein a clock radio member projects through the front wall, with radio controls directed through the first side wall, and an intermediate wall directed coextensively between the first side wall and the second side wall, and the top wall and the bottom wall defining a first chamber between the intermediate wall and the front wall, with the clock radio member mounted within the first chamber, and a partition wall extending from the intermediate wall to the rear wall, and from the first side wall to the second side wall, with a second chamber oriented between the partition wall and the bottom wall, and a third chamber oriented between the partition wall and the top wall, and dispensing means mounted within the third chamber for dispensing condom package units, and heating means for heating the third chamber, with the heating means mounted within the second chamber, and the dispensing means includes an abutment plate mounted between the second side wall and the first side wall, with an abutment plate spring directed between the abutment plate and the first side wall, with the abutment plate arranged for communication with said condom package units to direct the condom package units against the second side wall within the third chamber, and a top wall slot directed through the top wall in communication with the third chamber, wherein the slot is positioned in adjacency relative to the second side wall, with the top wall slot having a push bar, with the push bar including a push bar handle projecting through the top wall slot extending above the top wall, and at least one spring extending between the push bar and the top wall within the third chamber to bias the push bar in adjacency to the top wall within the third chamber, and a second side wall chute directed through the second side wall extending through the second side wall into communication with the partition wall, with the chute oriented below the top wall slot to receive one of the condom package units when the push bar is directed onto one of said condom package units.

2. An apparatus as set forth in claim 1 wherein the heating means includes a plurality of radiant heat lamps mounted within the second chamber arranged to receive electrical communication exteriorly of the second chamber to effect heating of the radiant heat lamps, with the partition wall having a plurality of partition wall apertures to receive heat from the second chamber into the third chamber, and a plurality of second side wall openings directed through the second side wall in communication with the second chamber to direct air flow into the second chamber.

3. An apparatus as set forth in claim 2 including a reservoir container mounted into the top wall, said reservoir container having a reservoir chamber formed of a heat transmissive material, and the reservoir container in communication with the third chamber, with the reservoir chamber including an aromatic fluid, with a lid member mounted to the reservoir container, said lid member having apertures therein to direct the aromatic fluid in a vaporized state through the lid member.

* * * * *